(12) United States Patent
McClurg

(10) Patent No.: US 8,576,985 B2
(45) Date of Patent: Nov. 5, 2013

(54) METHODS FOR INDEXING SOLID FORMS OF COMPOUNDS

(75) Inventor: Richard B. McClurg, West Lafayette, IN (US)

(73) Assignee: Aptuit (West Lafayette) LLC, Wilmington, DE (US)

( * ) Notice: Subject to any disclaimer, the term of this patent is extended or adjusted under 35 U.S.C. 154(b) by 652 days.

(21) Appl. No.: 12/871,421

(22) Filed: Aug. 30, 2010

(65) Prior Publication Data

US 2011/0054805 A1    Mar. 3, 2011

Related U.S. Application Data

(60) Provisional application No. 61/239,941, filed on Sep. 1, 2009.

(51) Int. Cl.
*G01N 23/207*    (2006.01)
*G01N 23/20*    (2006.01)
*G01N 23/00*    (2006.01)

(52) U.S. Cl.
USPC .................. 378/75; 378/73; 378/74

(58) Field of Classification Search
USPC ............... 378/70, 71, 73–75, 86, 88
See application file for complete search history.

(56) References Cited

FOREIGN PATENT DOCUMENTS

WO    WO 03100406 A1    12/2003

OTHER PUBLICATIONS

Neumann, M. A., J. Appl. Cryst. (2003) 36, 356-365. (English language abstract of article at http://journals.iucr.org/j/issues/2003/02/00/issconts.html).

*Primary Examiner* — Anastasia Midkiff
(74) *Attorney, Agent, or Firm* — O'Brien Jones PLLC

(57) ABSTRACT

The methods of the invention determine the unit cell parameters of a crystalline solid form using diffraction data and applying an algorithm. Using the algorithm, the unit cell parameters may be determined, which may allow one to distinguish between different crystalline solid forms of a substance.

14 Claims, 4 Drawing Sheets

METHODS FOR INDEXING SOLID FORMS OF COMPOUNDS

CROSS-REFERENCE TO RELATED APPLICATIONS

This application claims priority under 35 U.S.C. §119 to U.S. Provisional Application 61/238,941, filed Sep. 1, 2009, which is incorporated herein by reference.

TECHNICAL FIELD

The invention described herein relates to methods of characterizing solid forms, and methods of determining the unit cell of a crystalline solid form which may provide information about the solid form, for example to distinguish between different crystalline solid forms of a substance.

BACKGROUND

Diffraction is an experimental technique in which radiation with a narrow range of wavelengths is shone on a sample. The radiation interacts with the electrons and/or nuclei in the sample and is scattered elastically. Interference within the scattered radiation creates an observable pattern that is characteristic of the molecular-scale structure of the sample. To be effective, the radiation should have a wavelength that is similar to the atomic scale. For example, X-rays, high energy electrons, and thermal neutrons may be used. X-rays are readily produced using laboratory sources and are non-destructive at sufficiently low doses. Therefore, X-ray diffraction (XRD) is the most commonly used diffraction technique.

Single crystal diffraction is used to determine the molecular scale structure of a crystalline form of matter using a single crystal. Diffracted radiation is measured as a function of scattering angle and relative orientation of the crystal. Typically thousands of coherent peaks in the interference pattern are used to determine the size and shape of the crystal unit cell and the positions of each atom in the crystal. While very useful, the need for a large crystal with few defects limits the application of single crystal diffraction.

If only a powder sample (as opposed to a single crystal) is available, then powder diffraction may be used to obtain a sub-set of the information available using single crystal diffraction. For a sample composed of many tiny and randomly oriented particles, the resulting diffraction pattern has continuous rings instead of discrete points and the diffraction pattern is largely independent of the orientation of the sample. Due to overlap of the rings, typically dozens of coherent peaks in the interference pattern are measured as a function of scattering angle. If X-rays are used for the radiation and the sample is a powder, then the technique is called X-ray powder diffraction (XRPD). FIG. 1 provides a schematic view of XRPD. As noted above, alternate forms of radiation may also be used.

Although the invention set forth herein will be described primarily with respect to XRPD, it should be understood that other forms of powder diffraction, such as electron and neutron powder diffraction, can also be used.

The term "crystalline" as used herein includes polycrystalline, microcrystalline, nanocrystalline, and partially or wholly crystalline substances, as well as disordered crystalline substances. Crystalline solid forms can include, for example, cocrystals, solvates and hydrates. Crystalline solid forms can also include polymorphs, which are different crystalline solid forms having the same chemical composition. Crystalline solid forms can include crystalline forms of salts of compounds, for instance, salts of pharmaceutical compounds. In addition, as used herein reference to a crystalline solid form of "a compound" includes a crystalline solid form comprising a compound and optionally one or more additional compounds or components, i.e., a multi-component system. For instance, a crystalline solid form of a compound includes a cocrystal and includes a salt of a compound.

The result of XRPD is an XRPD pattern. For samples composed of crystalline powders, the XRPD pattern may be a combination of sharp peaks and broad features. Sharp peaks are due to ordered crystalline regions in the sample. The sharp peaks occur at particular scattering angles (2θ) relative to the transmitted X-ray beam. The broad features may be due to a variety of factors, such as disorder in the sample, defects in the crystal, and/or scattering by air.

The XRPD pattern is a measured intensity (I) as a function of scattering angle (2θ). The positions of the peaks in the pattern and the relative intensities of the peaks are characteristic of a well-prepared sample of a particular crystalline material. Therefore, an XRPD pattern identifies a particular material, just as a fingerprint identifies a particular person. For many purposes, the XRPD pattern can be used directly without additional analysis.

Powder diffraction data may also be used to determine the crystallographic unit cell of the crystalline structure. Many methods of powder diffraction indexing are known. XRPD indexing, and in fact indexing of all powder diffraction data, is the process of determining the size and shape of the crystallographic unit cell consistent with the peak positions in a given XRPD pattern. Indexing does not make use of the relative intensity information in the XRPD pattern. The goal of the indexing process is the determination of three unit cell lengths (a,b,c), three unit cell angles ($\alpha,\beta,\gamma$), and three Miller index labels (h,k,l) for each peak. The lengths are typically reported in Angstrom units (Å), and the angles in degree units. The Miller index labels are unitless integers. Successful indexing indicates that the sample is composed of one crystalline phase and is therefore not a mixture of crystalline phases. The indexing solution also provides a concise means to convey the positions of allowed peaks in an XRPD pattern. Other exemplary methods of powder diffraction indexing include, by way of example, Dicvol and X-cell, both of which are known to those of skill in the art.

Crystallographic unit cells are not unique. For any crystalline material, there is an infinite set of unit cells that may be used to describe the crystal structure of the material. There is, however, a unique unit cell called the reduced basis that has a minimal volume (V) and whose parameters (a,b,c,$\alpha,\beta,\gamma$) conform to a set of rules. The reduced basis provides a systematic means for categorizing and comparing crystal forms. Reduced bases conform to one of 44 tabulated "characters." Characters are a means of classification of reduced unit cells. Lattices belong to the same character if their reduced cells can be continuously deformed into one-another without changing the Bravais type and with continuous changes of the reduced lattice parameters. For each character there is a tabulated matrix transformation that generates a conventional unit cell from the reduced basis. The conventional cell parameters are most often reported as the outcome of XRPD indexing.

The invention makes use of an algorithm developed by the inventor, herein termed the "Triads Algorithm." By applying the Triads Algorithm to measured instrumental data, the benefits of the invention, as described below, may be achieved.

In the Triads Algorithm described below, the overall strategy is to identify a member of the infinite set of unit cells that describe the lattice, then use well-established methods to transform the cell to its reduced basis and finally to the conventional unit cell.

The Bragg Equation (1) relates the Bragg angle (θ) to the order of the reflection (n), the radiation wavelength (λ), and the distance between Miller planes ($d_{hkl}$):

$$n\lambda = 2d_{hkl}\sin(\theta) \quad (1)$$

Rearranging equation (1) provides an equation for the scattering vector magnitude ($\kappa_{hkl}$):

$$\kappa_{hkl} = \frac{2\sin(\theta)}{\lambda} = \frac{n}{d_{hkl}} \quad (2)$$

Although the symbol k is often used for the magnitude of the scattering vector, here the symbol κ is used to avoid confusion with the Miller indices (h,k,l). The distance between Miller planes ($d_{hkl}$) is a function of the Miller indices (h,k,l) and the crystallographic unit cell parameters (a,b,c,α,β,γ). This function is most conveniently expressed using matrix multiplication:

$$(\kappa_{hkl})^2 = [h\ k\ l] \cdot \underline{B} \cdot \begin{bmatrix} h \\ k \\ l \end{bmatrix} \quad (3)$$

where B is the Bragg matrix:

$$\underline{B} = \begin{bmatrix} (a^*)^2 & (a^*)(b^*)\cos(\gamma^*) & (a^*)(c^*)\cos(\beta^*) \\ (a^*)(b^*)\cos(\gamma^*) & (b^*)^2 & (b^*)(c^*)\cos(\alpha^*) \\ (a^*)(c^*)\cos(\beta^*) & (b^*)(c^*)\cos(\alpha^*) & (c^*)^2 \end{bmatrix} \quad (4)$$

and (a*,b*,c*,α*,β*,γ*) are reciprocal cell parameters. Equations (3) and (4) constitute the quadratic form of the Bragg Equation. It gives the peak position for a given Miller index triplet (h,k,l) given a unit cell of specified reciprocal cell parameters.

Simplified versions of the quadratic form are available for symmetric crystal systems. These simplifications are special cases of the general triclinic case provided in equations (3) and (4). Since the triclinic case is general, it is used in the implementation of the Triads Algorithm described below. Higher symmetry unit cells are recognized during the course of the algorithm.

Friedel's Law states that peaks labeled with Miller indices (h,k,l) and (−h,−k,−l) are indistinguishable in the absence of absorption effects. Slight deviations from Friedel's Law are used in the context of single crystal diffraction to determine absolute configuration of chiral molecules, but this is not relevant to XRPD since the opposing pairs of peaks overlap each other in an XRPD pattern. Since Friedel pairs always overlap in XRPD patterns, it is convenient to choose a naming convention that eliminates this ambiguity. In a preferred embodiment of the present invention, all Miller indices may be chosen such that the first non-zero index is positive. This embodiment is used in the examples below. In a further embodiment, all Miller indices may be chosen such that the first non-zero index is negative. In yet a further embodiment, a combination of positive and negative first non-zero Miller indices may be chosen.

Each of the infinite set of unit cells that describe a particular crystalline material yields reflections at the same set of peak positions (2θ) through the Bragg Equation. Larger unit cells will indicate additional peaks that are not indicated for a minimal volume unit cell, however. Since different unit cells have different unit cell parameters, the Miller indices labeling each peak are also different, but the set of distances between Miller planes is fixed. An example illustrating the equivalence of different unit cells is given in TABLE 1.

TABLE 1

Exemplary comparison of Miller index labels for three different unit cells describing the same crystal with the same peak positions.

| Observed Peak Positions (2θ) | Arbitrarily Specified Cell<br>a = 10.000 Å, b = 17.321 Å,<br>c = 26.458 Å, α = 10.89°<br>β = 55.46° γ = 54.74°<br>(Triclinic) | Reduced Basis<br>a = b = c = 10.000 Å,<br>α = β = γ = 60°<br>(Rhombohedral) | Conventional Cell<br>a = b = c = 14.142 Å,<br>α = β = γ = 90°<br>(Face-Centered Cubic) |
|---|---|---|---|
| 10.827° | (100), (123), (011), (012) | (001), (010), (100), (111) | (111) |
| 12.508° | (112), (023), (111) | (011), (101), (110) | (002), (020), (200) |
| 17.724° | (1-1-1), (223), (135), (134), (1-1-2), (001) | (01-1), (10-1), (1-10), (112), (121), (211) | (022), (202), (220) |
| 20.815° | (212), (034), (1-2-3), (2, 3, 5), (101), (146), (035), (124), (234), (211), (122), (10-1) | (11-1), (1-11), (1-1-1), (021), (201), (210), (012), (102), (120), (122), (212), (221) | (113), (131), (311) |
| 21.752° | (200), (246), (022), (024) | (002), (020), (200), (222) | (222) |
| 25.168° | (224), (046), (222) | (022), (202), (200) | (004), (040), (400) |

For each of three different unit cells, Miller indices are given for each of the observed peaks. In TABLE 1 there are multiple Miller indices corresponding to each peak. This is a result of multiple lattice planes that diffract at the same Bragg angle and therefore overlap in the XRPD pattern. Such coincidence of reflections is common for symmetric unit cells such as the one used in TABLE 1. Each column in TABLE 1 is a different description of the same unit cell, but with different unit cell parameters and Miller index labels for the observed peaks. This demonstrates that there are multiple indexing solutions (column 1, for instance), any one of which may be reduced to the reduced basis (column 2) and then transformed to the conventional cell (column 3). This allows one to assign Miller indices in a convenient fashion, for example during the generation of trial solutions during the Triads Algorithm. Once the Algorithm generates a unit cell that is consistent with the observed peak list, then the cell can be reduced and transformed to the conventional cell.

SUMMARY

The invention described herein relates to the characterization of crystalline solid forms. In accordance with exemplary embodiments of the invention, the inventor has discovered novel methods for determining the unit cell parameters of a crystalline solid form in a process known as indexing. In various embodiments of the invention, one or more diffraction methods are used to obtain data for a crystalline solid form, an algorithm is applied to obtain unit cell parameters, and the peaks in the XRPD pattern are indexed.

One exemplary embodiment of the invention is a method for determining the crystal unit cell parameters of a crystalline solid form, comprising generating an X-ray powder diffraction pattern of a solid crystalline substance and determining the unit cell parameters of the substance by performing the Triads Algorithm to identify one or more sets of values of unit cell parameters of the crystalline solid form. Further exemplary embodiments may include one or more refinement steps.

In at least one embodiment, the methods of the invention may be applied, for example, to distinguish between different crystalline solid forms of a substance.

BRIEF DESCRIPTION OF THE DRAWINGS

The accompanying figures illustrate various exemplary embodiments of the invention and, together with the description, serve to further illustrate certain principles of the invention.

DESCRIPTION OF EXEMPLARY EMBODIMENTS

Figure 1:
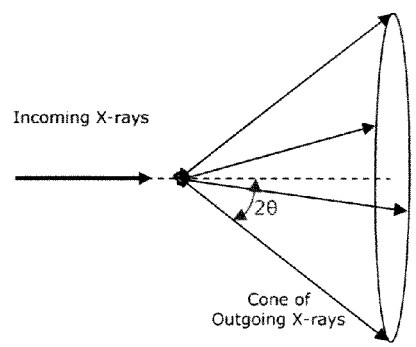
FIG. 1 illustrates a schematic view of X-ray powder diffraction (XRPD)

Reference will now be made in greater detail to exemplary embodiments of the invention. It is to be understood that both the foregoing general description and following detailed description are exemplary and explanatory only, and are not to be interpreted as restrictive of the invention as claimed. It will be apparent to one skilled in the art that the invention may be practiced without some or all of these specific details, and the disclosure is intended to cover alternatives, modifications, and equivalents. For example, well-known features and/or process steps may not have been described in detail so as not to unnecessarily obscure the invention.

This invention relates to the characterization of crystalline solid forms. The invention includes methods for determining the unit cell parameters of a crystalline solid form by using an indexing algorithm referred to as the Triads Algorithm.

Crystalline solid forms may be generated in numerous ways. For example, samples may be crystallized in different environments by, for instance, using different solvents, different temperatures, different humidities, or different pressures. Such different conditions increase the likelihood of obtaining more than one crystalline solid form of a compound.

An indexed unit cell can, in various embodiments, be used to determine the relationship between different crystalline solid forms of a single molecule. For example, it can assist in determining whether the crystalline solid forms are iso-structural and/or part of a single hydrate family. Indexing can be used to rule out erroneous claims of new forms arising from, for example, poor particle statistics or preferred orientation artifacts. If an indexed crystal unit cell describes all measured diffraction peaks in a powder pattern, then most likely the sample material has the same crystal unit cell.

The indexing method of the invention may be applied, for example, to distinguish between different crystalline solid forms of a substance. This method may be used, for example, in a screen for identifying new crystalline solid forms of a substance. The ability to index a measured powder pattern may also rule out the possibility that the sample material is a mixture of different crystalline solid forms. The inverse can also be true. If a powder pattern cannot be indexed, then the sample material may be a mixture of different crystalline solid forms, which is another source of false form identification.

The Triads Algorithm allows for the identification of members of the infinite set of crystallographic unit cells that describes a given XRPD pattern, without regard for whether or not those cells conform to conventions for their proper description. In other words, a convenient, rather than conventional, unit cell can be determined. In certain embodiments of the invention, known methods may be used to reduce an arbitrary unit cell to the reduced basis or for transforming the reduced basis to the conventional unit cell. The Triads Algorithm may be more useful than other methods in certain applications, such as, for example, low symmetry crystal structures such as those commonly found for molecular solids.

In one embodiment, the method selects three sets of three peaks, called Triads, in such a way as to generate unit cells that may describe a particular XRPD pattern. Although some of the peaks may appear in more than one triad, up to six peaks from the XRPD pattern may be used to generate a candidate unit cell. Additional peaks may be needed to verify the candidate unit cell.

In the following description, step numbers correspond to labels in FIGS. 2A and 2B:

Step 1:

In a first step of an embodiment of the Triads Algorithm method of the invention, an X-ray powder diffractometer may generate one or more XRPD patterns of a crystalline solid form. FIG. 2A, 1. Examples of such diffractometers include any such instruments known in the art including, for example, the Siemens D-500 X-ray Powder Diffractometer-Kristalloflex and a Shimadzu XRD-6000 X-ray powder diffractometer. A common choice is to use Cu—Kα radiation, but Mo and other metal anodes may also be used.

Step 2:

Once XRPD patterns of the crystalline solid form are generated, a peak list may then be prepared corresponding to the XPRD pattern. FIG. 2A, 2. Typically, the peak list indicates scattering angles (2θ[deg]) at which higher than background intensity is observed. In one embodiment, low-angle peaks, regardless of intensity, may be selected. The term "low-angle" is well known in the art and refers to peaks with values of $\kappa$ that are within the ranges specified by equation (5) below. Since these ranges may be dependent upon the selected basis peaks, it is difficult to provide an upper limit on the range for low-angle peaks. For low-angle basis peaks (Step 4), the specified vector sum ranges are also for relatively low-angle peaks. Inclusion of higher angle peaks in the observed peak list does not interfere with the success of the algorithm and may, in some embodiments, aid in solution refinement (Steps 10, 13, 16, and 18). Longer observed peak lists necessitate longer calculated peak lists (Step 8) which may extend the total execution time for the algorithm. One of skill in the art will generally appreciate which peaks are considered "low-angle" for any particular sample.

Figure 3:
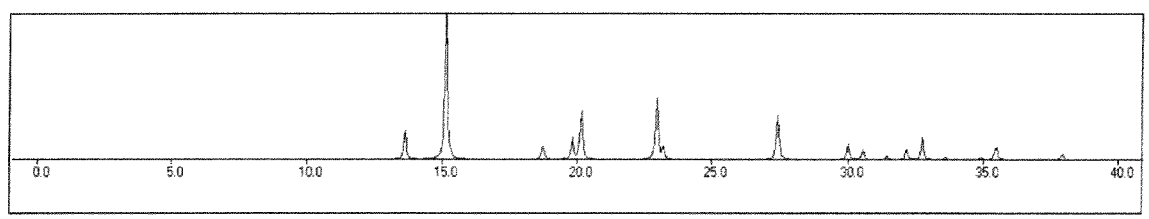
FIG. 3 illustrates an XRPD pattern calculated from the Cambridge Structural Database structure ABIVIQ, using the wavelength of Cu—Kα radiation.

Step 3:

It is convenient to express the peak list as a function of $\sin(\theta)$, $\kappa[1/\text{Å}]$, $\kappa^2[1/\text{Å}^2]$, and/or $d/n$ [Å] where $\kappa$ is the magnitude of the scattering vector and $d/n$ is the distance between Miller planes divided by the order of the reflection (See equation 2), and $\lambda$ is the wavelength of the incident X-ray radiation. For example, $\lambda$ is 1.54059 Å for Cu—K$\alpha_1$ radiation. FIG. 2A, 3.

Figure 4:
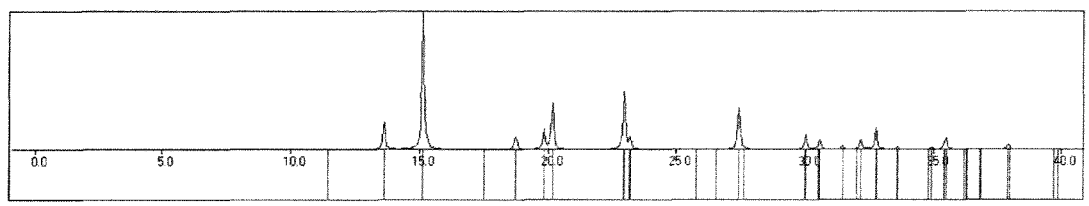
FIG. 4 illustrates the XRPD pattern of FIG. 3 with bars below the axis to indicate the positions of reflections calculated using Bragg's Law and the reciprocal cell parameters generated using the Triads Algorithm.

Step 4:

In a further step of an embodiment of the Triads Algorithm method of the invention, three peaks from the peak list are chosen and labeled as A, B, and C. FIG. 2A, 4. In the following description, these three peaks are called basis peaks. The basis peaks may be chosen in any order. It is convenient to select the peaks in a way that avoids permutations of the labels since such permutations do not lead to independent indexing solutions. For example, the peaks may be chosen such that $\kappa_C \leq \kappa_B \leq \kappa_A$.

Step 5:

Next, in a further step of an embodiment of the Triads Algorithm method of the invention, peaks in the XRPD pattern, and thus the peak list, may be determined for the vector sums of pairs of C, B, and A, within the following ranges of equation (5):

$$|\kappa_B - \kappa_C| \leq \kappa_{B+C} \leq \kappa_B + \kappa_C$$

$$|\kappa_A - \kappa_C| \leq \kappa_{A+C} \leq \kappa_A + \kappa_C$$

$$|\kappa_A - \kappa_B| \leq \kappa_{A+B} \leq \kappa_A + \kappa_B \tag{5}$$

Figure 2A:
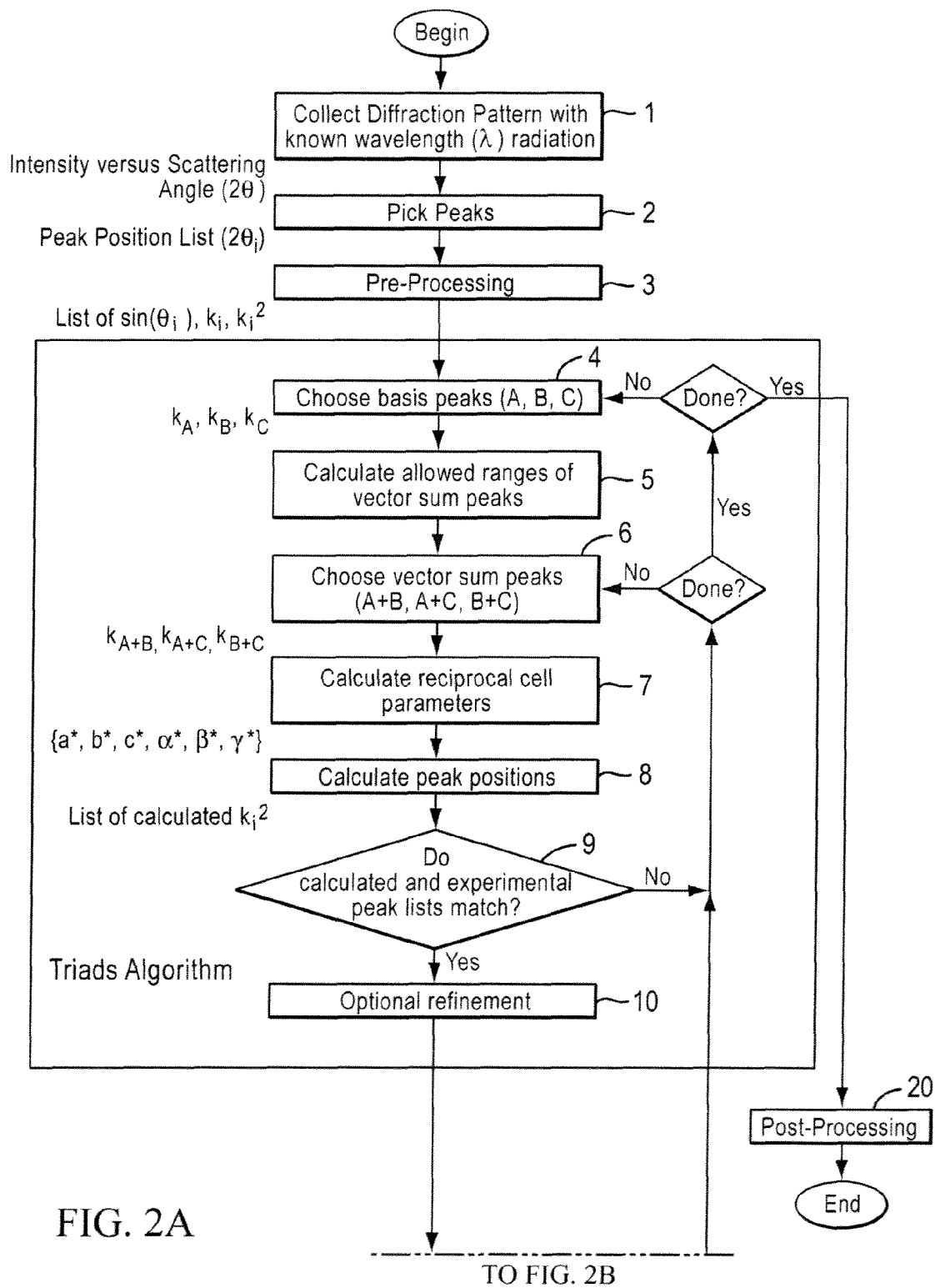
FIGS. 2A-2B provide a flowchart of steps for implementing the Triads Algorithm and associated procedures, where the steps of the Triads Algorithm are set out in the box in FIG. 2A.
Figure 2B:
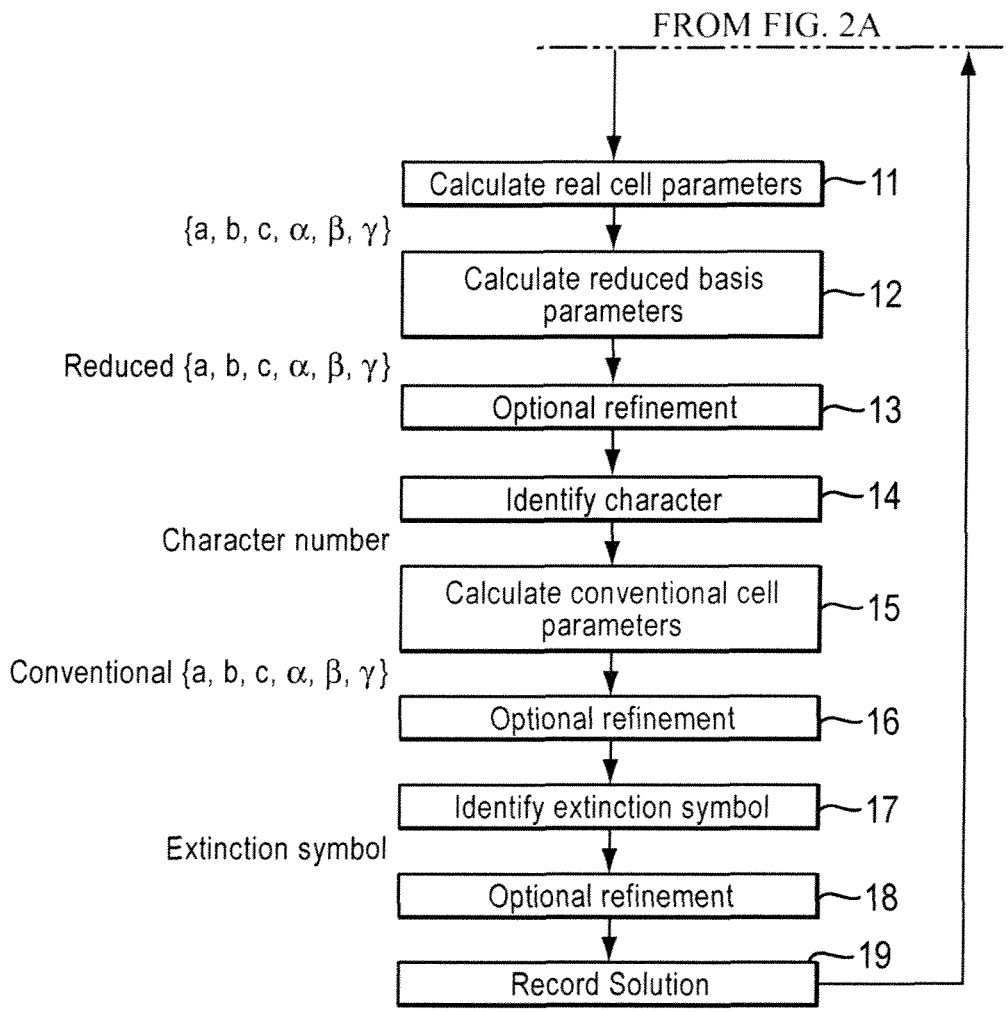
Figure 5:
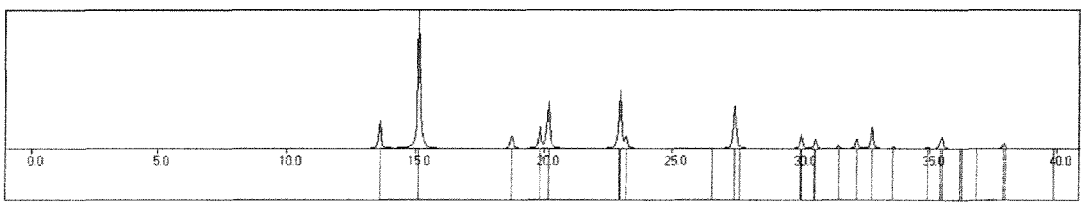
FIG. 5 illustrates the XRPD pattern of FIG. 3 with bars below the axis to indicate the positions of reflections for the conventional unit cell and extinction symbol.

FIG. 2A, 5. The indicated ranges follow from the interpretation of $\kappa_{X+Y}$ as a vector sum of $\kappa_X$ and $\kappa_Y$, where X and Y are selected from A, B, and C. Since the reciprocal angle cosines in equation (4) are bounded on −1 to +1, it follows that the magnitude of the vector sum peaks are bounded by the sum and difference of the component vectors. Since B, C, and B+C appear together in equation (5), they are termed a Triad which is the origin of the name of the algorithm. Note that the absolute magnitude indicated in equation (5) is redundant if the basis peaks are assigned as indicated in Step 4.

Step 6:

In a further step of an embodiment of the Triads Algorithm method of the invention, three peaks from the peak list within the ranges specified in Step 5 are chosen and labeled as B+C, A+C, and A+B. FIG. 2A, 6.

Step 7:

In a further step of an embodiment of the Triads Algorithm method of the invention, the reciprocal cell length parameters $(a^*, b^*, c^*)$ can be calculated from $\kappa_C$, $\kappa_B$, and $\kappa_A$ based on the assignment of the Miller index labels of (001), (010), and (100), respectively. FIG. 2A, 7. This can be done by methods known to those of skill in the art. Note that this portion of Step 7 may be accomplished following Step 4 above. This is efficient since the basis peaks remain fixed while the vector sum peaks are repeatedly chosen and tested.

$$\begin{bmatrix} (1/\Delta\kappa_A^2) & 0 & 0 \\ 0 & (1/\Delta\kappa_B^2) & 0 \\ 0 & 0 & (1/\Delta\kappa_C^2) \end{bmatrix} \cdot \begin{bmatrix} (a^*)^2 \\ (b^*)^2 \\ (c^*)^2 \end{bmatrix} = \begin{bmatrix} \kappa_A^2/\Delta\kappa_A^2 \\ \kappa_B^2/\Delta\kappa_B^2 \\ \kappa_C^2/\Delta\kappa_C^2 \end{bmatrix} \tag{6}$$

In a further step of an embodiment of the Triads Algorithm method of the invention, the cosines of the reciprocal cell angle parameters $(\alpha^*, \beta^*, \gamma^*)$ can be calculated from $\kappa_{B+C}$, $\kappa_{A+C}$, and $\kappa_{A+B}$, under the assumption that their Miller index labels are (011), (101), and (110), respectively.

$$\begin{bmatrix} \left(\frac{2}{\Delta\kappa_{B+C}^2}\right) & 0 & 0 \\ 0 & \left(\frac{2}{\Delta\kappa_{A+C}^2}\right) & 0 \\ 0 & 0 & \left(\frac{2}{\Delta\kappa_{A+B}^2}\right) \end{bmatrix} \cdot \begin{bmatrix} b^* c^* \cos(\alpha^*) \\ a^* c^* \cos(\beta^*) \\ a^* b^* \cos(\gamma^*) \end{bmatrix} = \tag{7}$$

$$\left(\begin{bmatrix} \left(\frac{\kappa_{B+C}^2}{\Delta\kappa_{B+C}^2}\right) \\ \left(\frac{\kappa_{A+C}^2}{\Delta\kappa_{A+C}^2}\right) \\ \left(\frac{\kappa_{A+B}^2}{\Delta\kappa_{A+B}^2}\right) \end{bmatrix} - \begin{bmatrix} 0 & \left(\frac{1}{\Delta\kappa_{B+C}^2}\right) & \left(\frac{1}{\Delta\kappa_{B+C}^2}\right) \\ \left(\frac{1}{\Delta\kappa_{A+C}^2}\right) & 0 & \left(\frac{1}{\Delta\kappa_{A+C}^2}\right) \\ \left(\frac{1}{\Delta\kappa_{A+B}^2}\right) & \left(\frac{1}{\Delta\kappa_{A+B}^2}\right) & 0 \end{bmatrix} \cdot \begin{bmatrix} (a^*)^2 \\ (b^*)^2 \\ (c^*)^2 \end{bmatrix}\right)$$

Assignment of convenient Miller indices to selected peaks is permissible in the Triads Algorithm because of the non-uniqueness of crystallographic unit cells. By assigning the Miller index label (100) to peak A, the Algorithm is selecting a subset from the infinite set of equivalent unit cells. Assignment of Miller indices to the other peaks similarly selects subsets of equivalent unit cells. The intersection of these sets may be a null set indicating that new choices of basis peaks (A, B, and C) and/or vector sum peaks (B+C, A+C, and A+B) are needed. For some choices of basis peaks and vector sum peaks, the Triads Algorithm generates candidate unit cells. By construction, those cells are consistent with the six selected basis and vector sum peaks. The cells may then be evaluated to assess their consistency with the remaining peaks in the peak list.

Step 8:

The candidate unit cell generated using the Triads Algorithm may then be evaluated to determine if the cell is consistent with the entire peak list. FIG. 2A, 8. The first step is to calculate a peak list from the unit cell. This may be done, for example, by constructing a Bragg Matrix (B) from the calculated reciprocal cell parameters generated via the Triads Algorithm, as in equation (4), and then carrying out the indicated matrix multiplications in equation (3) for a series of Miller index triples (hkl). Sufficient ranges of the Miller indices are estimated from the reciprocal cell parameters. For the Miller index h, the maximum requisite value is given by:

$$h^{max} = \left\lfloor \frac{\kappa^{max}\sin(\alpha^*)}{\alpha^*\left(\frac{1-\cos^2(\alpha^*)-\cos^2(\beta^*)-\cos^2(\gamma^*)+}{2\cos(\alpha^*)\cos(\beta^*)\cos(\gamma^*)}\right)^{\frac{1}{2}}} \right\rfloor \quad (8)$$

where $\lfloor f \rfloor$ denotes the floor function applied to f, and $\kappa^{max}$ is the maximum value of $\kappa$ for the peak list. Equation (8) may be expressed more simply using real cell parameters instead of reciprocal cell parameters:

$$h^{max} = \lfloor a\kappa^{max} \rfloor \quad (9)$$

Analogous equations for $k^{max}$ and $l^{max}$ can be obtained using the following substitutions:
To calculate $k^{max}$,

| Symbol in equation (8) | Replacement |
| --- | --- |
| a* | b* |
| b* | a* |
| c* | unchanged |
| α* | β* |
| β* | α* |
| γ* | unchanged | or using real cell parameters:

$$k^{max} = \lfloor b\kappa^{max} \rfloor. \quad (10)$$

To calculate $l^{max}$,

| Symbol in equation (8) | Replacement |
| --- | --- |
| a* | c* |
| b* | unchanged |
| c* | a* |
| α* | γ* |
| β* | unchanged |
| γ* | α* | or using real cell parameters:

$$l^{max} = \lfloor c\kappa^{max} \rfloor. \quad (11)$$

The relevant ranges for (h,k,l) are $-h^{max} \leq h \leq h^{max}$, and similarly for k and l. Note the comments regarding Friedel's Law following equation (4) above may be used to further limit the sufficient domains in keeping with a particular choice of naming conventions.

Step 9:

In various exemplary embodiments, all of the observed peaks will be indexed by the candidate unit cell with appropriate choices of Miller indices. FIG. 2A, 9. In a few cases there are extra allowed reflections that are either extinct or just very weak, but all of the observed peaks may, for example, correspond to one or more Miller index triplets. In exemplary embodiments where all observed peaks are indexed by the trial unit cell and there are relatively few extra peaks, the trial unit cell is considered further. In exemplary embodiments where the agreement is unsatisfactory, then alternative choices for labeled peaks (A, B, C, A+B, A+C, and B+C) would be generated and evaluated.

Step 10:

The Triads Indexing Algorithm is well suited for unit cell parameter refinement. FIG. 2A, 10. The three basis peaks (A, B, and C) and three vector sum peaks (B+C, A+C, and A+B) form a linearly independent basis for determining the six reciprocal cell parameters as demonstrated in equations (6) and (7) of Step 7. For refinement, these six peaks are augmented with observed peaks whose positions are consistent with one and only one calculated peak, within their combined uncertainties. Such peaks are called Uniquely Indexed Peaks (UIPs). The union of the sets of basis peaks, vector sum peaks, and UIPs form a set of n peaks to be used in the refinement step. The coefficient matrix A, unknown vector x, and constant vector b are defined as follows:

$$\underline{A} = \begin{bmatrix} \left(\frac{h_1^2}{\Delta\kappa_1^2}\right) & \left(\frac{k_1^2}{\Delta\kappa_1^2}\right) & \left(\frac{l_1^2}{\Delta\kappa_1^2}\right) & \left(\frac{2k_1l_1}{\Delta\kappa_1^2}\right) & \left(\frac{2h_1l_1}{\Delta\kappa_1^2}\right) & \left(\frac{2h_1k_1}{\Delta\kappa_1^2}\right) \\ \vdots & \vdots & \vdots & \vdots & \vdots & \vdots \\ \left(\frac{h_n^2}{\Delta\kappa_n^2}\right) & \left(\frac{k_n^2}{\Delta\kappa_n^2}\right) & \left(\frac{l_n^2}{\Delta\kappa_n^2}\right) & \left(\frac{2k_nl_n}{\Delta\kappa_n^2}\right) & \left(\frac{2h_nl_n}{\Delta\kappa_n^2}\right) & \left(\frac{2h_nk_n}{\Delta\kappa_n^2}\right) \end{bmatrix} \quad (12)$$

$$\underline{x}^t = \quad (13)$$
$$[(a^*)^2 \ (b^*)^2 \ (c^*)^2 \ b^*c^*\cos(\alpha^*)^2 \ a^*c^*\cos(\beta^*)^2 \ a^*b^*\cos(\gamma^*)^2]$$

$$\underline{b}^t = \left[\left(\frac{\kappa_1^2}{\Delta\kappa_1^2}\right) \ \cdots \ \left(\frac{\kappa_n^2}{\Delta\kappa_n^2}\right)\right] \quad (14)$$

$$\underline{A} \cdot \underline{x} \approx \underline{b} \quad (15)$$

Note that there are at least six rows in A and b corresponding to the basis and vector sum peaks. UIPs, if not already included, add additional rows. There are precisely six columns in A and six rows in x corresponding to the six unknown reciprocal lattice parameters. The '$\approx$' sign in equation (15) recognizes that the system is over specified if UIPs have been used to augment A and b. Therefore, the solution for x is understood to be the optimal solution in a least-squares sense.

Note that equations (6) and (7) are special cases of equations (12) through (15).

Solution of equation (15) is readily accomplished using the "Normal Equation Method." The Covariance matrix (C) is calculated from the coefficient matrix (A) as follows:

$$\underline{C} = (\underline{A}^t \cdot \underline{A})^{-1} \quad (16)$$

then the best solution for x is given by:

$$\underline{x} \approx \underline{C} \cdot \underline{A}^t \cdot \underline{b} \quad (17)$$

The '$\approx$' sign in equation (17) is in recognition that the solution for x is a least-squares estimate.

Once the vector (x) is known, the position of any Bragg reflection with Miller Indices $(h_i, k_i, l_i)$ is estimated by:

$$\underline{v}_i^t = [h_i^2 k_i^2 l_i^2 2k_il_i 2h_il_i 2h_ik_i] \quad (18)$$

$$\kappa_i^2 \approx \underline{v}_i^t \cdot \underline{x} \quad (19)$$

and the uncertainty in the Bragg position is:

$$\Delta\kappa_i^2 \approx (\underline{v}_i^t \cdot \underline{C} \cdot \underline{v}_i)^{1/2} \quad (20)$$

Expanding equations (3) and (19) proves that they are equivalent.

Augmenting the Triads peaks with uniquely indexed peaks (if any) often results in smaller uncertainties in the Bragg positions. In turn, this leads to additional UIPs. Thus the peak list comparison (Step 9) and refinement (Step 10) may be applied iteratively until the list of UIPs is unchanged upon successive applications of the refinement process or the observed and calculated peak lists are found to be inconsistent.

Step 11:
In a further step of an exemplary embodiment of the invention, real space cell parameters may then be calculated. FIG. 2B, 11. This may be done by any method known to those of skill in the art.

Step 12:
In a further step of an exemplary embodiment, the reduced basis may then be calculated, as the real unit cell generally does not correspond to standard conventions. FIG. 2B, 12. This may be done by any method known to those of skill in the art.

Although the reduced basis is unique, it may not immediately convey the symmetry of many unit cells. Thus, in a further step of various additional embodiments of the invention, the conventional unit cell may be calculated. Conventional unit cells are constructed to convey the underlying cell symmetry more readily. To construct the conventional unit cell, the character number for the reduced basis is identified and the indicated cell transformation is applied. Methods for doing so are known to those of skill in the art.

Step 13:
Using the reduced basis, the low-angle Bragg reflections are labeled with small Miller indices. This is often not the case for the unit cell prior to the cell reduction (Step 12). Since the Miller indices (h,k,l) for individual reflections change upon reduction, the corresponding coefficient matrix A in equation (12) and covariance matrix C in equation (16) also change. As a result, the calculated uncertainty for a particular peak, $\Delta \kappa^2$, changes as a result of unit cell reduction. Modified peak position estimates may lead to additional UIPs which justifies another round of refinement. The process is the same as described in Step 10, except that the Miller indices must refer to the reduced cell basis.

If the unit cell prior to the cell reduction has a matrix representation M and the transformation matrix for the cell reduction is T, then the matrix representation of the reduced basis is given by:

$$\underline{M}_{reduced} = \underline{M} \cdot \underline{T} \qquad (21)$$

The same transformation matrix converts the Miller indices from the original basis to the reduced basis:

$$\begin{bmatrix} h \\ k \\ l \end{bmatrix}_{reduced} = \underline{T}^t \cdot \begin{bmatrix} h \\ k \\ l \end{bmatrix} \qquad (22)$$

The Miller indices (h,k,l) in the reduced basis are used in the refinement process. FIG. 2B, 13.

Step 14:
Once the reduced basis has been determined, the character corresponding to the reduced basis is determined by comparison with tabulated descriptions. International Tables for Crystallography, Vol A, 5$^{th}$ ed., §9.2, pp. 750-755. FIG. 2B, 14.

Step 15:
For each character there is a corresponding matrix transformation that converts the reduced basis to the conventional unit cell. FIG. 2B, 15. Application of the matrix transformation is similar to that in equation (21).

Step 16:
Following conversion to the conventional unit cell, the Miller indices for individual reflections must be converted to the conventional unit cell basis. Transforming the Miller indices from the reduced basis to the conventional basis is similar to that in equation (22). For similar reasons to those given in Step 13, this justifies another round of cell refinement which uses the conventional cell Miller indices, but is otherwise similar to that described in Step 10. FIG. 2B, 16.

Step 17:
In further exemplary embodiments of the invention, additional processing steps may also be performed. By way of non-limiting example, in certain cases the extinction symbol may be applied such as when systemic extinctions due to additional symmetry of the unit cell contents exist. FIG. 2B, 17. In those cases, applying the extinction symbol may give shorter calculated peak lists that match the observed peak list with fewer unobserved peaks. In these cases the extinction symbol indicates the presence of glide planes and/or screw axes in the crystal structure. Note that cell centering, which also yields systematic extinctions, had already been recognized in Step 15 as part of the conventional unit cell construction.

Step 18:
Since application of extinction symbols may eliminate reflections that had interfered with the identification of UIPs, a final round of refinement may be warranted. FIG. 2B, 18.

Step 19:
Most trial solutions do not reach step 19 since they are found to be inconsistent in Step 9 or in one of the refinement steps (Steps 10, 13, 16, or 18). The trial solutions that do survive to Step 19 are consistent with the observed peak list, but not all consistent trial solutions are optimal. Solutions with fewer calculated peaks, more uniquely indexed peaks, and smaller peak uncertainties are often considered preferred solutions than more complex and/or less accurate solutions, and thus are favorable. Therefore, trial solutions reaching Step 19 are evaluated, compared with previously generated trial solutions, and recorded if the solutions are judged to be favorable. FIG. 2B, 19.

Step 20:
As discussed above, indexing results can be used to distinguish or screen crystalline solid forms such as pharmaceuticals. Therefore, an additional exemplary embodiment of the invention comprises comparing structural information obtained for different crystalline solid samples, such as the indexed unit cell, to determine whether XRPD patterns of those samples represent the same or different crystalline solid forms. FIGS. 2A-2B, 20.

This embodiment can comprise, for example, comparing structural information obtained for different crystalline solid samples, such as the results obtained from the method of the invention, to determine whether XRPD patterns of those samples represent the same or different crystalline solid forms. The calculation of the same crystal unit cell parameters can indicate that the samples have the same crystalline solid form. Conversely, the calculation of different crystal unit cell parameters for samples represented by different XRPD patterns can indicate that the samples do not have the same crystalline solid form. One of skill in the art, evaluating the results of the methods described herein, can determine whether two samples represent the same or different forms, based on knowledge and techniques that are well known.

Another embodiment of the invention comprises sorting, screening, or ranking various crystalline solid forms on the basis of certain structural information specific to the forms, such as, for example, the unit cell parameters, character, and/or extinction symbol of each crystalline solid form. For instance, the invention comprises methods of screening for new crystalline solid forms of a substance, which comprises determining structural information for a plurality of crystalline samples of a substance using the embodiments described above, comparing the structural information of the samples to structural information of known crystalline solid forms of the substances, and identifying those crystalline samples that have structural information different from that of the known crystalline solid forms.

It should be noted that the terms "same" or "similar," as used herein, such as, for example, when referring to unit cell parameters, are meant to convey that a particular set of data is, within acceptable scientific limits, sufficiently similar to another such that one of skill in the art would appreciate that the data represent, for example, the same crystalline solid form of a compound. In this regard, and as is commonly practiced within the scientific community, it is not intended that the data be identical in order to be considered the same or similar.

The present invention is further illustrated by the following non-limiting examples, which are provided to further aid those of skill in the art in the appreciation of the invention.

It is noted that, as used in this specification and the appended claims, the singular forms "a," "an," and "the," include plural referents unless expressly and unequivocally limited to one referent, and vice versa. Thus, by way of example only, reference to "a crystalline solid form" can refer to one or more crystalline solid forms, and reference to "a compound" can refer to one or more compounds. As used herein, the term "include" and its grammatical variants are intended to be non-limiting, for example such that recitation of items in a list is not to the exclusion of other like items that can be substituted or added to the listed items.

It will be apparent to those skilled in the art that various modifications and variations can be made to the present disclosure without departing from the scope of its teachings. Other embodiments of the disclosure will be apparent to those skilled in the art from consideration of the specification and practice of the teachings disclosed herein, such as, for example, the use of the methods herein with powder diffraction data other than XRPD data. It is intended that the embodiments described in the specification be considered as exemplary only. Additional objects and advantages of the invention are set forth in the following description. For instance, it will be noted that the order of the steps presented need not necessarily be performed in that order set forth herein to practice the invention, and some steps may be changed or omitted all together.

EXAMPLES

Example 1

In the following example, which is not intended to be limiting of the invention as claimed, the Triads Algorithm is applied to a crystalline material whose structure is stored in the Cambridge Structural Database (CSD), with the ABIVIQ reference code. The corresponding molecule is 1,4-Dimethyl-2,5-dioxabicyclo(2.2.1)heptane-3,6-dione. Its crystal structure was previously determined. In other words, Example 1 uses simulated data obtained from the CSD, rather than experimentally-obtained data, in order to demonstrate the accuracy and precision of the methods of the invention.

Step 1:

As an initial step, the XRPD pattern for ABIVIQ was calculated to approximate an experimental XRPD pattern measured using Cu—Kα radiation. The pattern was calculated using the MERCURY software package. The calculated XRPD pattern is presented in FIG. 3.

Steps 2-4:

Next, the following peak list of TABLE 2 was generated by picking peaks from the XRPD pattern of FIG. 3 and calculating corresponding values for $\sin(\theta)$ and the scattering vector magnitude ($\kappa$) for each peak. Three peaks were selected and labeled as A, B, and C. The indicated peaks were selected for the example because they lead to a correct indexing solution. Most choices for basis peaks A, B, and C do not lead to correct indexing solutions, but the illustrated choice is not unique either.

TABLE 2

Peak list for ABIVIQ generated from XRPD pattern of FIG. 3 with basis peaks (A, B, and C) labeled.

| 2θ [deg] | sin(θ) | κ [1/Å] | Label |
|---|---|---|---|
| 13.62 | 0.1186 | 0.1539 | C |
| 15.12 | 0.1316 | 0.1708 | B |
| 18.74 | 0.1628 | 0.2114 | A |
| 19.84 | 0.1723 | 0.2236 | |
| 20.16 | 0.1750 | 0.2272 | |
| 22.96 | 0.1990 | 0.2584 | |
| 23.20 | 0.2011 | 0.2610 | |
| 27.42 | 0.2370 | 0.3077 | |
| 30.02 | 0.2590 | 0.3362 | |
| 30.54 | 0.2634 | 0.3419 | |
| 31.44 | 0.2709 | 0.3517 | |
| 32.14 | 0.2768 | 0.3594 | |
| 32.74 | 0.2818 | 0.3659 | |
| 33.58 | 0.2889 | 0.3750 | |
| 34.90 | 0.2999 | 0.3893 | |

Step 7 (Partial):

Next, the following reciprocal cell length parameters (a*, b*, c*) were calculated from $\kappa_C$, $\kappa_B$, and $\kappa_A$ on the assumption that their Miller index labels are (001), (010), and (100), respectively:

$$c^* = \kappa_C = 0.1539/\text{Å}$$

$$b^* = \kappa_B = 0.1708/\text{Å}$$

$$a^* = \kappa_A = 0.2114/\text{Å}$$

Step 5:

Subsequently, peaks for the vector sums of pairs C, B, and A were determined within the ranges of equation (5). For the current example, $\kappa_B = 0.1708/\text{Å}$ and $\kappa_C = 0.1539/\text{Å}$. Therefore:

$$0.0169/\text{Å} = \kappa_B - \kappa_C \leq \kappa_{B+C} \leq \kappa_B + \kappa_C = 0.3247/\text{Å}$$

There are eight candidate peaks within the specified range in the XRPD pattern of FIG. 2. Similarly, since $\kappa_A = 0.2114/\text{Å}$:

$$0.0575/\text{Å} = \kappa_A - \kappa_C \leq \kappa_{A+C} \leq \kappa_A + \kappa_C = 0.3653/\text{Å}$$

$$0.0406/\text{Å} = \kappa_A - \kappa_B \leq \kappa_{A+B} \leq \kappa_A + \kappa_B = 0.3822/\text{Å}$$

There are twelve candidate peaks within the specified range for A+C and fourteen candidate peaks within the specified range for A+B.

Step 6:

Accordingly, there are 8*12*14=1344 combinations of triads of the form $\{\kappa_B, \kappa_C, \kappa_{B+C}\}$, $\{\kappa_A, \kappa_C, \kappa_{A+C}\}$, $\{\kappa_A, \kappa_B, \kappa_{A+B}\}$ for the choice of basis peaks (A, B, and C) and the peak list provided in TABLE 2. One such combination is indicated in TABLE 3:

TABLE 3

Peak list for ABIVIQ from TABLE 2 with vector sum peaks (B + C, A + C, and A + B) labeled.

| 2θ [deg] | sin(θ) | κ [1/Å] | Label |
|---|---|---|---|
| 13.62 | 0.1186 | 0.1539 | C |
| 15.12 | 0.1316 | 0.1708 | B |
| 18.74 | 0.1628 | 0.2114 | A |
| 19.84 | 0.1723 | 0.2236 | |
| 20.16 | 0.1750 | 0.2272 | A + B |
| 22.96 | 0.1990 | 0.2584 | B + C |
| 23.20 | 0.2011 | 0.2610 | |
| 27.42 | 0.2370 | 0.3077 | |
| 30.02 | 0.2590 | 0.3362 | A + C |
| 30.54 | 0.2634 | 0.3419 | |
| 31.44 | 0.2709 | 0.3517 | |
| 32.14 | 0.2768 | 0.3594 | |
| 32.74 | 0.2818 | 0.3659 | |
| 33.58 | 0.2889 | 0.3750 | |
| 34.90 | 0.2999 | 0.3893 | |

Step 7 (Continued):

Further, the cosines of the reciprocal cell angle parameters ($\alpha^*, \beta^*, \gamma^*$) were calculated from $\kappa_{B+C}$, $\kappa_{A+C}$, and $\kappa_{A+B}$ with the assigned Miller index labels (011), (101), and (110), respectively:

$$\cos(\alpha^*) = \frac{(\kappa_{B+C})^2 - (b^*)^2 - (c^*)^2}{2b^*c^*} = 0.2641$$

$$\cos(\beta^*) = \frac{(\kappa_{A+C})^2 - (a^*)^2 - (c^*)^2}{2a^*c^*} = 0.6865$$

$$\cos(\gamma^*) = \frac{(\kappa_{A+B})^2 - (a^*)^2 - (b^*)^2}{2a^*b^*} = -0.3077$$

TABLE 4

Reciprocal space unit cell parameters calculated for ABIVIQ (initial cell).

| | |
|---|---|
| a* = | 0.2114 Å$^{-1}$ |
| b* = | 0.1708 Å$^{-1}$ |
| c* = | 0.1539 Å$^{-1}$ |
| cos(α*) = | 0.2641 |
| cos(β*) = | 0.6865 |
| cos(γ*) = | −0.3077 |
| V* = | 0.002793 Å$^{-3}$ |

The reciprocal cell volume (V*) is similar in magnitude to $(k_1)^3 = 0.003648/Å^3$. If the reciprocal cell volume had been much smaller than $(k_1)^3$ then the trial solution would be rejected since such a cell would have too many calculated peaks to be judged acceptable in Step 19. Since the trial cell reciprocal volume and the estimate are similar in magnitude, the algorithm continues with Step 8.

Step 8:

Next, the trial unit cell was evaluated by constructing the Bragg Matrix (B) from the calculated reciprocal cell parameters and equations (3) and (4). FIG. 4 shows that all of the observed peaks are indexed by the candidate unit cell with appropriate choices of Miller indices. The bars below the axis indicate the positions of reflections calculated using Bragg's Law and the reciprocal cell parameters generated using the Triads Algorithm. In a few cases there are extra allowed reflections that are not evident, either because they are extinct or just very weak, but all of the observed peaks correspond to one or more Miller index triplets. Since all observed peaks were indexed by the trial unit cell and there are relatively few extra peaks, the trial unit cell is further evaluated. If the agreement had been unsatisfactory, then alternative choices for labeled peaks (A, B, C, A+B, A+C, and B+C in TABLE 2) could have been generated and evaluated.

Step 9:

Since there is at least one calculated peak position (Step 8) for each observed peak (Step 2) then the peak lists are judged to match and the algorithm continues with Step 10 below.

Step 10:

For the current example and at this stage of the algorithm, the only UIP is also the A basis peak. Since there are no additional peaks beyond those already used in the calculation of the reciprocal lattice parameters, there is no benefit from the refinement step. Therefore, this refinement step is skipped.

Step 11:

Next, the real space parameters were calculated using methods known in the art.

TABLE 5

Real space unit cell parameters calculated for ABIVIQ (unconventional cell).

| | |
|---|---|
| a = | 9.079 Å |
| b = | 8.470 Å |
| c = | 12.298 Å |
| α = | 133.41° |
| β = | 146.79° |
| γ = | 45.78° |

Step 12:

Subsequently, the reduced basis was calculated using methods known in the art.

TABLE 6

Reduced basis real parameters calculated for ABIVIQ.

| | |
|---|---|
| a = | 6.843 Å |
| b = | 6.849 Å |
| c = | 8.470 Å |
| α = | 71.81° |
| β = | 71.96° |
| γ = | 81.46° |

Despite the change in lattice parameters and Miller index labels, the peak positions illustrated in FIG. 4 are unchanged by the basis reduction procedure.

Step 13:

For the current example and at this stage of the algorithm, there are two UIPs: one basis peak and one other. The second UIP facilitates refinement of the reciprocal lattice parameters of the reduced basis. It is used to augment the coefficient matrix (A) and the vector (b). The resulting reciprocal lattice parameters are:

TABLE 7

Refined reduced basis reciprocal parameters calculated for ABIVIQ.

| | |
|---|---|
| a* = | 0.1539 Å$^{-1}$ |
| b* = | 0.1538 Å$^{-1}$ |
| c* = | 0.1293 Å$^{-1}$ |
| cos(α*) = | −0.2816 |
| cos(β*) = | −0.2819 |
| cos(γ*) = | −0.0565 |
| V* = | 0.002787 Å$^{-3}$ |

Step 14:

Converting the reciprocal parameters in TABLE 7 to real space, using the same method as in Step 11, and then comparing with tabulated character descriptions leads to the conclusion that the reduced basis conforms to character 10, within reasonable round-off errors.

Step 15:

This allows the conventional unit cell to be determined by applying the indicated cell transformation for character 10, which generates a centered monoclinic conventional unit cell with the following parameters using methods known in the art. The requisite matrix transformations are tabulated and the procedure for applying the matrix transformation is documented elsewhere.

TABLE 8

Conventional cell parameters calculated for ABIVIQ.

| Cell | C-Centered |
|---|---|
| a = | 10.378 Å |
| b = | 8.944 Å |
| c = | 8.478 Å |
| α = | 90.00° |
| β = | 114.25° |
| γ = | 90.00° |

Despite the change in parameters and Miller index labels, the allowed peak positions illustrated in FIG. 4 are unchanged. The parameters listed in TABLE 8 conform to the usual monoclinic conventional cell definition (with α=γ=90°) which is not evident in the reduced basis of TABLE 6.

Step 16:

Optional refinement using reciprocal lattice parameters for conventional cell leads to the slightly different conventional cell parameters listed in TABLE 9.

TABLE 9

Refined conventional cell parameters calculated for ABIVIQ.

| Cell | C-Centered |
|---|---|
| a = | 10.376 Å |
| b = | 8.944 Å |
| c = | 8.477 Å |
| α = | 90.00° |
| β = | 114.24° |
| γ = | 90.00° |

Step 17:

Some of the allowed peak positions labeled with bars below the axis in FIG. 4 do not correspond to observed peaks. This may be the result of peaks that are too weak or may be due to systematic extinctions due to additional symmetry of the unit cell contents. An extinction symbol was sought using methods known to those of skill in the art to account for as many of these unobserved peaks as possible while maintaining consistency with the observed peaks. Such techniques can be applied to determine that the systematic extinctions are consistent with the monoclinic C1c1 extinction symbol. Applying that extinction symbol gives the allowed peak positions illustrated in FIG. 5. The excellent agreement in peak positions with a lack of unobserved peaks indicates that the conventional unit cell and extinction symbol are an acceptable indexing solution for the XRPD pattern.

Step 18:

Optional refinement using reciprocal lattice parameters for the conventional cell and applied extinction symbol leads to the values tabulated in the leftmost column of TABLE 10. The middle column contains the conventional cell parameters in the CSD entry used to construct the XRPD pattern in Step 1. The rightmost column contains their difference.

TABLE 10

Refined conventional cell parameters calculated for ABIVIQ with extinction symbol determination.

| | Triads Algorithm | CSD: ABIVIQ | Difference |
|---|---|---|---|
| | Extinction Symbol | | |
| | C1c1 | C1c1 | n/a |
| a = | 10.376 Å | 10.379 Å | −0.003 Å |
| b = | 8.944 Å | 8.943 Å | −0.001 Å |
| c = | 8.477 Å | 8.477 Å | 0.000 Å |
| α = | 90.00° | 90° | 0° |
| β = | 114.24° | 114.22° | −0.02° |
| γ = | 90.00° | 90° | 0° |
| V = | 717.4 Å$^3$ | 717.57 Å$^3$ | 0.2 Å$^3$ |

Step 19:

TABLE 11 summarizes the ten highest ranked solutions generated with the Triads indexing algorithm and various choices of basis and vector sum peaks. The table compares them to the known unit cell parameters for ABIVIQ. The top row is the trial solution detailed above.

TABLE 11

Ten equivalent unit cell determinations for ABIVIQ compared with the known solution.

| A | B | C | B + C | A + C | A + B | a [Å] | b [Å] | c [Å] | α [deg] | β [deg] | γ [deg] | V [Å$^3$] |
|---|---|---|---|---|---|---|---|---|---|---|---|---|
| 3 | 2 | 1 | 6 | 9 | 5 | 10.3762 | 8.9445 | 8.4775 | 90 | 114.237 | 90 | 717.4 |
| 4 | 2 | 1 | 6 | 1 | 2 | 10.3764 | 8.9444 | 8.4776 | 90 | 114.239 | 90 | 717.4 |
| 4 | 2 | 1 | 6 | 11 | 12 | 10.3769 | 8.9444 | 8.4775 | 90 | 114.239 | 90 | 717.5 |
| 5 | 1 | 1 | 4 | 6 | 13 | 10.3759 | 8.9443 | 8.4775 | 90 | 114.236 | 90 | 717.4 |
| 5 | 2 | 1 | 6 | 13 | 10 | 10.3760 | 8.9445 | 8.4777 | 90 | 114.233 | 90 | 717.5 |
| 5 | 3 | 1 | 1 | 13 | 2 | 10.3754 | 8.9446 | 8.4775 | 90 | 114.233 | 90 | 717.4 |
| 5 | 3 | 1 | 9 | 6 | 2 | 10.3762 | 8.9445 | 8.4775 | 90 | 114.237 | 90 | 717.4 |
| 5 | 4 | 1 | 1 | 6 | 5 | 10.3759 | 8.9443 | 8.4775 | 90 | 114.235 | 90 | 717.4 |

TABLE 11-continued

Ten equivalent unit cell determinations for ABIVIQ compared with the known solution.

| A | B | C | B + C | A + C | A + B | a [Å] | b [Å] | c [Å] | α [deg] | β [deg] | γ [deg] | V [Å$^3$] |
|---|---|---|---|---|---|---|---|---|---|---|---|---|
| 5 | 4 | 1 | 1 | 13 | 5 | 10.3754 | 8.9446 | 8.4775 | 90 | 114.233 | 90 | 717.4 |
| 5 | 4 | 1 | 11 | 6 | 15 | 10.3769 | 8.9444 | 8.4775 | 90 | 114.239 | 90 | 717.5 |
| Mean | | | | | | 10.3761 | 8.9445 | 8.4775 | 90 | 114.236 | 90 | 717.43 |
| ABIVIQ | | | | | | 10.379 | 8.943 | 8.477 | 90 | 114.22 | 90 | 717.57 |
| Difference | | | | | | −0.0029 | 0.0015 | 0.0005 | 0 | 0.016 | 0 | −0.14 |
| % diff | | | | | | −0.03% | 0.02% | 0.01% | n/a | 0.01% | n/a | −0.02% |

Step 20:

TABLE 11 demonstrates that the algorithm has yielded duplicate, highly ranked solutions which are in agreement with the known correct solution. While such duplicates are not necessary, they are indicative of a successful indexing solution. Successful indexing solution provides evidence of a single crystalline phase and a concise description of the peak positions in its XRPD pattern.

Example 2

In the following example, which is not intended to be limiting of the invention as claimed, the Triads Algorithm is applied to a crystalline sample of mannitol, form beta. Example 2 uses experimentally-obtained data.

A XRPD pattern was acquired using a PANalytical X'Pert Pro diffractometer. An incident beam of Cu Kα radiation was produced using an Optix long, fine-focus source. An elliptically graded multilayer mirror was used to focus the Cu Kα X-rays of the source through the specimen and onto the detector. Data were collected and analysed using X'Pert Pro Data Collector software (v. 2.2b). Prior to the analysis, a silicon specimen (NIST SRM 640c) was analyzed to verify the instrument alignment using the Si 111 peak position. The specimen was sandwiched between 3 μm thick films, analyzed in transmission geometry, and rotated to optimize orientation statistics. A beam-stop was used to minimize the background generated by air scattering. Soller slits were used for the incident and diffracted beams to minimize axial divergence. Diffraction patterns were collected using a scanning position-sensitive detector (X'Celerator) located 240 mm from the specimen.

A peak list was constructed with 35 observed peaks and the Triads Algorithm was carried out. The results are given in TABLE 12. Excellent agreement between the Triads Algorithm results and previously reported indexing results demonstrates the ability of the algorithm to successfully index experimental data, in addition to the simulated XRPD pattern used in Examples 1 and 3. The differences in lattice parameters are slightly larger in Example 2 than in Examples 1 and 3, probably due to differences in the samples and/or conditions of the analyzed samples. It is because of this uncertainty that a simulated XRPD pattern was used to assess the accuracy and precision of the algorithm in Examples 1 and 3.

TABLE 12

Two representative indexing solutions for Mannitol, form beta compared with a published structure.

| | a [Å] | b [Å] | c [Å] | α [deg] | β [deg] | γ [deg] | V [Å$^3$] | Space Group |
|---|---|---|---|---|---|---|---|---|
| | 5.5491 | 8.6768 | 16.9039 | 90 | 90 | 90 | 813.90 | P2$_1$2$_1$2$_1$ (#19) |
| | 5.5491 | 8.6768 | 16.9039 | 90 | 90 | 90 | 813.90 | P2$_1$2$_1$2$_1$ (#19) |
| Mean | 5.5491 | 8.6768 | 16.9039 | 90 | 90 | 90 | 813.896 | n/a |
| DMANTL04[1] | 5.549 | 8.672 | 16.890 | 90 | 90 | 90 | 812.762 | P2$_1$2$_1$2$_1$ (#19) |
| Difference | 0.0001 | 0.0048 | 0.0138 | 0 | 0 | 0 | 1.134 | n/a |
| % diff | 0.0018 | 0.055 | 0.082 | n/a | n/a | n/a | 0.14 | n/a |

[1]The lattice parameters are sorted according to reduced cell convention for comparison.

Example 3

In the following example, which is not intended to be limiting of the invention as claimed, the Triads Algorithm is applied to a set of XRPD patterns collected from the CSD. Example 3 uses simulated data, which demonstrates that the methods of the invention are broadly applicable to all of the 44 reduced bases or characters.

The set includes representatives of each of the 44 characters with a few duplicates. Characters 20 and 31 contain duplicates for a total of 46 structures. The algorithm accurately identified 44 of 46 indexing solutions. For AABHTZ and ABACUC, the indexing solutions were assigned to centered monoclinic rather than triclinic solutions. This is a problem common to all indexing routines since indexing routines determine metric symmetry and are therefore insensitive to the symmetry of the cell contents. In both of the problematic structures, the reduced cell (Step 12) provides the correct triclinic unit cell. Packing of the molecular contents would be necessary to correctly identify the triclinic unit cell as the correct indexing solution in these cases. For the other 44 indexing solutions, the rms fractional error in unit cell lengths was 0.022% and the rms error in unit cell angles was 0.0090 degrees. Thus, the indexing of the invention provided agreement to the source structure unit cell parameters with excellent precision and accuracy. The small residual errors are the result of rounding errors in the peak positions selected in Step 2.

TABLE 13

List of CSD structures used to test the Triads Indexing Algorithm.

| Char. # | Bravais | Type | CSD ID | SG | | Ext. Symb |
|---|---|---|---|---|---|---|
| 1 | c | F | GIGRIX | Fm-3m | 255 | F - - - |
| 2 | h | R | AZTPHZ01 | R-3 | 148 | R - - |
| 3 | c | P | BZCBNL05 | Pa-3 | 205 | P a - - |
| 4 | h | R | ASXANT01 | R-3 | 148 | R - - |
| 5 | c | I | BIGLUZ | I-43m | 217 | I - - - |
| 6 | t | I | BAYJIU | I41/a | 88 | I 41/a - - |
| 7 | t | I | ACAVIJ | I41/a | 88 | I 41/a - - |
| 8 | o | I | FABGOE | Iba2 | 45 | I c - a |
| 9 | h | R | FIDJOS | R-3 | 148 | R - - |
| 10 | m | C | ABIVIQ | C2/c | 15 | C 1 c 1 |
| 11 | t | P | ACNORT | P41212 | 92 | P 41 21 - |
| 12 | h | P | BODROB | P63/m | 176 | P 63 - - |
| 13 | o | C | BERCUW | C2221 | 20 | C - - 21 |
| 14 | m | C | ABUBEE | C2/c | 15 | C 1 c 1 |
| 15 | t | I | GOLCAL | I41/a | 88 | I 41/a - - |
| 16 | o | F | ALUVAE | F2dd | 43 | F - d d |
| 17 | m | C | ABIXUF | C2/c | 15 | C 1 c 1 |
| 18 | t | I | AGURAV | I41/a | 88 | I 41/a - - |
| 19 | o | I | ARIRAU | Iba2 | 45 | I c - a |
| 20 | m | C | ABUNAM | C2/c | 15 | C 1 c 1 |
| 20 | m | C | ACXHTZ | C2/c | 15 | C 1 c 1 |
| 21 | t | P | CAPINC | P41212 | 92 | P 41 21 - |
| 22 | h | P | BARBOL | P63/m | 176 | P 63 - - |
| 23 | o | C | TASKON | C2221 | 20 | C - - 21 |
| 24 | h | R | BELQOZ | R-3 | 148 | R - - |
| 25 | m | C | ABOMEJ | C2/c | 15 | C 1 c 1 |
| 26 | o | F | ARAGUV | Fdd2 | 43 | F - d d |
| 27 | m | C | ABIHOI | C2/c | 15 | C 1 c 1 |
| 28 | m | C | BAPMAH | C2/c | 15 | C 1 c 1 |
| 29 | m | C | AMAQUA | C2/c | 15 | C 1 c 1 |
| 30 | m | C | BESCIM | C2/c | 15 | C 1 c 1 |
| 31 | a | P | AABHTZ | P-1 | 2 | P - |
| 31 | a | P | ABACAI | P-1 | 2 | P - |
| 32 | o | P | ABELAV | P212121 | 19 | P 21 21 21 |
| 33 | m | P | POVJIT | P21/c | 14 | P 1 21/c 1 |
| 34 | m | P | POXHDO | P21/n | 14 | P 1 21/n 1 |
| 35 | m | P | POVKEQ | P21/n | 14 | P 1 21/n 1 |
| 36 | o | C | PFBIPH01 | C2221 | 20 | C - - 21 |
| 37 | m | C | ACEGUL | C2/c | 15 | C 1 c 1 |
| 38 | o | C | WAVYAU | C2221 | 20 | C - - 21 |
| 39 | m | C | ACIBIX | C2/c | 15 | C 1 c 1 |
| 40 | o | C | LABTAK | C2221 | 20 | C - - 21 |
| 41 | m | C | AKADIZ | C2/c | 15 | C 1 c 1 |
| 42 | o | I | CIHCUR01 | Iba2 | 45 | I c - a |
| 43 | m | I | BAWPOE | I2/c | 15 | I 1 a 1 |
| 44 | a | P | ABACUC | P-1 | 2 | P - |

What is claimed is:

1. A method for determining the unit cell parameters of a crystalline solid form of a compound, which method comprises:
   i. using a diffractometer to generate powder diffraction data for a solid crystalline substance; and
   ii. determining the unit cell parameters of the substance by performing a Triads Algorithm to identify one or more sets of values of unit cell parameters of the crystalline solid form.

2. A method as in claim 1, which further comprises performing one or more refinement steps.

3. A method as in claim 1, wherein the powder diffraction data is processed by the following step after it is obtained and prior to the application of the Triads Algorithm:

a. generating a peak list from the powder diffraction data of the crystalline solid substance, wherein said peak list includes the following data obtained from the powder diffraction data:
   i. $2\theta$[deg];
   ii. $\sin(\theta)$;
   iii. $\kappa$[1/Å];
   iv. $\kappa^2$[1/Å$^2$] and/or
   v. $d/n$ [Å],
where $\kappa = 2\sin(\theta)/\lambda$ and $d/n = 1/\kappa$.

4. A method as in claim 3, wherein the Triads Algorithm, comprising the following steps, is performed:
   b. choosing three basis peaks from the peak list and labeling them A, B, and C;
   c. using (001), (010), and (100), respectively, as Miller indices, to calculate the reciprocal cell length parameters (a*,b*,c*) from $\kappa_C$, $\kappa_B$, and $\kappa_A$;
   d. determining acceptable ranges for the vector sums of pairs of C, B, and A using any of the following ranges:

$$\kappa_B - \kappa_C \leq \kappa_{B+C} \leq \kappa_B + \kappa_C, \quad \text{i.}$$

$$\kappa_A - \kappa_C \leq \kappa_{A+C} \leq \kappa_A + \kappa_C, \text{ and} \quad \text{ii.}$$

$$\kappa_A - \kappa_B \leq \kappa_{A+B} \leq \kappa_A + \kappa_B; \quad \text{iii.}$$

e. choosing three peaks from the ranges in (d) and labeling as B+C, A+C, and A+B;
   f. using (011), (101), and (110), respectively, as Miller indices, to calculate the cosines of the reciprocal cell angle parameters of ($\alpha^*,\beta^*,\gamma^*$) from $\kappa_{B+C}$, $\kappa_{A+C}$, and $\kappa_{A+B}$;
   g. calculating peak positions; and
   h. determining whether the cell is consistent with the entire peak list.

5. A method as in claim 4, wherein step (c) is performed after step (e) rather than after step (b).

6. A method as in claim 4, comprising the further step of (i) refining the unit cell parameters.

7. A method as in claim 6, further comprising one or more steps chosen from evaluating the trial unit cell, calculating the real space unit cell, calculating the reduced basis, calculating the conventional unit cell, and identifying the extinction symbol.

8. A method as in claim 6, further comprising one or more of the following steps:
   j. calculating the real space cell parameters;
   k calculating the reduced basis parameters;
   l. refining the reduced basis parameters;
   m. identifying the character corresponding to the reduced basis;
   n. calculating the conventional cell parameters;
   o. refining the conventional cell parameters;
   p. applying the extinction symbol;
   q. evaluating the solution and recording if favorable; and
   r post-processing the data.

9. A method as in claim 8, wherein post-processing the data comprises comparing the data to data from a second crystal form to determine whether the two samples represent the same or different crystal forms.

10. A method as in claim 9, comprising the steps of:
   i. indexing powder diffraction data from two different samples; and
   ii. comparing extinction symbols and/or numerical values for the unit cell parameters for each sample.

11. A method for determining the unit cell parameters of a crystalline solid form of a compound, which method comprises using an X-ray powder diffractometer to generate XRPD data for a solid crystalline substance; and
- a. generating a peak list from the XRPD data of the crystalline solid substance;
- b. choosing three basis peaks and labeling them A, B, and C;
- c. using (001), (010), and (100), respectively, as Miller indices, to calculate the reciprocal cell length parameters (a*,b*,c*) from $\kappa_C$, $\kappa_B$, and $\kappa_A$;
- d. determining acceptable ranges for the vector sums of pairs of C, B, and A using any of the following ranges:

i. $\kappa_B - \kappa_C \leq \kappa_{B+C} \leq \kappa_B + \kappa_C$, ii. $\kappa_A - \kappa_C \leq \kappa_{A+C} \leq \kappa_A + \kappa_C$, and iii. $\kappa_A - \kappa_B \leq \kappa_{A+B} \leq \kappa_A + \kappa_B$;

- e. choosing three peaks from the ranges in (d) and labeling as B+C, A+C, and A+B;
- f. using (011), (101), and (110), respectively, as Miller indices, to calculate the cosines of the reciprocal cell angle parameters of ($\alpha^*,\beta^*,\gamma^*$) from $\kappa_{B+C}$, $\kappa_{A+C}$, and $\kappa_{A+B}$;
- g. calculating peak positions;
- h. determining whether the cell is consistent with the entire peak list; and
- i. refining the unit cell parameter.

12. A method as in claim 11, further comprising one or more of the following steps:

- l. calculating the real space cell parameters;
- k. calculating the reduced basis parameters;
- l. refining the reduced basis parameters;
- m. identifying the character corresponding to the reduced basis;
- n. calculating the conventional cell parameters;
- o. refining the conventional cell parameters;
- p. applying the extinction symbol;
- q. evaluating the solution and recording if favorable; and
- r. post-processing the data.

13. A method for distinguishing between crystalline solid forms of different samples of a substance, which comprises: for each sample, generating an X-ray powder diffraction pattern of a solid crystalline substance; determining the unit cell parameters of each substance by performing a Triads Algorithm to identify one or more sets of values of unit cell parameters of the crystalline solid forms, and comparing the one or more sets of values of unit cell parameters of the crystalline solid forms.

14. A method of sorting, screening, or ranking crystalline solid forms, which comprises: for each sample, generating an X-ray powder diffraction pattern of the solid crystalline form; determining the unit cell parameters of the substance by performing a Triads Algorithm to identify one or more sets of values of unit cell parameters of the crystalline solid form, and sorting, screening, or ranking the crystalline solid forms based on the unit cell parameters, character, and/or extinction symbol of each crystalline solid form.

* * * * *

UNITED STATES PATENT AND TRADEMARK OFFICE
CERTIFICATE OF CORRECTION

PATENT NO. : 8,576,985 B2  
APPLICATION NO. : 12/871421  
DATED : November 5, 2013  
INVENTOR(S) : Richard B. McClurg Page 1 of 1

It is certified that error appears in the above-identified patent and that said Letters Patent is hereby corrected as shown below:

On the Title Page, item 60 "Related U.S. Application Data", "61/239,941" should read --61/238,941--.

Signed and Sealed this  
Twenty-eighth Day of January, 2014

Michelle K. Lee  
*Deputy Director of the United States Patent and Trademark Office*